United States Patent
Li et al.

(10) Patent No.: US 11,786,734 B2
(45) Date of Patent: Oct. 17, 2023

(54) IMPLANTABLE LEAD MIGRATION MONITORING USING ECAP

(71) Applicant: Medtronic, Inc., Minneapolis, MN (US)

(72) Inventors: Jiashu Li, Mounds View, MN (US); David A. Dinsmoor, North Oaks, MN (US); Duane L. Bourget, Andover, MN (US); Kristin N. Hageman, Dayton, MN (US); Hank Bink, Golden Valley, MN (US); Christopher L. Pulliam, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/988,144

(22) Filed: Aug. 7, 2020

(65) Prior Publication Data

US 2022/0040485 A1 Feb. 10, 2022

(51) Int. Cl.
*A61N 1/36* (2006.01)
*A61N 1/372* (2006.01)
(Continued)

(52) U.S. Cl.
CPC .......... *A61N 1/36139* (2013.01); *A61B 5/068* (2013.01); *A61B 5/746* (2013.01);
(Continued)

(58) Field of Classification Search
None
See application file for complete search history.

(56) References Cited

U.S. PATENT DOCUMENTS 9,381,357 B2 7/2016 Min et al.
9,713,720 B2 7/2017 Zhu
(Continued)

FOREIGN PATENT DOCUMENTS

WO 2019204884 A1 10/2019

OTHER PUBLICATIONS

Gmel et al., "Electrophysiological Responses of the S3 Sacral Nerve in Humans During Neuromodulation for Faecal Incontinence," European Society of Coloproctology, Sep. 2018, 1 pg.
(Continued)

*Primary Examiner* — Paula J Stice
(74) *Attorney, Agent, or Firm* — Shumaker & Sieffert, P.A.

(57) ABSTRACT

Systems, devices, methods, and techniques are described for using evoked compound action potential (ECAP) signals to monitor lead position and/or detect lead migration. An example system includes sensing circuitry configured to sense an ECAP signal, and processing circuitry. The processing circuitry controls the sensing circuitry to detect, after delivery of an electrical stimulation pulse, a current ECAP signal, and determines one or more characteristics of the current ECAP signal. The processing circuitry also compares the one or more characteristics of the current ECAP signal to corresponding one or more characteristics of a baseline ECAP signal, and determines, based on the comparison, a migration state of the electrodes delivering the electrical stimulation pulse. Additionally, the processing circuitry outputs, based on the migration state, an alert indicative of migration of the electrodes.

24 Claims, 12 Drawing Sheets

(51) Int. Cl.
   *A61B 5/06* (2006.01)
   *A61B 5/00* (2006.01)

(52) U.S. Cl.
   CPC ..... *A61N 1/36125* (2013.01); *A61N 1/36135* (2013.01); *A61N 1/37235* (2013.01); *A61N 1/36171* (2013.01); *A61N 1/36175* (2013.01)

(56) References Cited

U.S. PATENT DOCUMENTS

| | | | |
|---|---|---|---|
| 10,183,168 B2 | 1/2019 | Baru et al. | |
| 2014/0163639 A1* | 6/2014 | Zhu | A61N 1/0551 607/46 |
| 2014/0296737 A1* | 10/2014 | Parker | A61B 5/4836 600/554 |
| 2015/0360031 A1* | 12/2015 | Bornzin | A61N 1/36071 607/62 |
| 2017/0259065 A1* | 9/2017 | Baru | A61N 1/36125 |
| 2019/0142325 A1 | 5/2019 | Min et al. | |
| 2019/0175904 A1* | 6/2019 | Baru | A61N 1/0551 |
| 2019/0209844 A1* | 7/2019 | Esteller | A61N 1/36132 |

OTHER PUBLICATIONS

U.S. Appl. No. 16/721,576, filed Dec. 19, 2019, naming inventors Dinsmoor et al.

IEEE Standards Association; IEEE Standard for Information technology—Telecommunications and information exchange between systems; Local and metropolitan area networks—Specific requirements; "Part 11: Wireless LAN Medium Access Control (MAC) and Physical Layer (PHY) Specifications. Amendment 3: Enhancements for Very High Throughput in the 60 GHz Band," IEEE Computer Society; Sponsored by the LAN/MAN Standards Committee; IEEE Standard 802.11ad™-2012 (Amendment to IEEE Std 802.11™-2012, as amended by IEEE Std 802.11ae™-2012 and.

International Search Report and Written Opinion of International Application No. PCT/US2021/044262, dated Nov. 22, 2021, 9 pp.

* cited by examiner

IMPLANTABLE LEAD MIGRATION MONITORING USING ECAP

TECHNICAL FIELD

This disclosure generally relates to medical devices, and more specifically, determining changes to the position of implanted electrodes.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device.

SUMMARY

In general, systems, devices, and techniques are described for using evoked compound action potential (ECAP) signals to monitor lead position to detect lead migration. When an implantable medical device (IMD) is implanted, leads are implanted at a location to provide suitable stimulation. The IMD delivers a pulse with a pulse width and frequency to sense an ECAP and establish a baseline ECAP signal that establishes the characteristics of the ECAP signals when the leads are appropriately positioned. From time-to-time (e.g., hourly, daily, weekly, etc.), the IMD may sense one or more ECAP signals elicited by an amplitude sweep of pulses with a defined pulse width and frequency. The IMD may compare a characteristic of the sensed ECAP signals against a characteristic of a baseline ECAP signal. In some examples, the IMD accounts for posture of the patient (e.g., as collected by an inertial sensor of the IMD, etc.). For example, the IMD may delay taking an ECAP measurement when the posture of the patient is indicative of an unreliable ECAP measurement. If one or more characteristics of the collected ECAP change by a threshold amount compared to the corresponding characteristics of the baseline ECAP signal, the IMD may determine that the lead has migrated. In response to this trigger of lead migration, for example, the IMD may adjust stimulation provided by the lead, or request another device or user to adjust stimulation, to compensate for the migration of the lead from the previously detected implant location.

An example system includes sensing circuitry configured to sense an ECAP signal, and processing circuitry. The processing circuitry controls the sensing circuitry to detect, after delivery of an electrical stimulation pulse, a current ECAP signal, and determines one or more characteristics of the current ECAP signal. The processing circuitry also compares the one or more characteristics of the current ECAP signal to corresponding one or more characteristics of a baseline ECAP signal, and determines, based on the comparison, a migration state of the electrodes delivering the electrical stimulation pulse. Additionally, the processing circuitry outputs, based on the migration state, an alert indicative of migration of the electrodes.

An example method to detect migration of leads coupled to an implantable medical device, the method includes detecting, via sensing circuitry, after delivery of an electrical stimulation pulse, a current ECAP signal, and determining, by processing circuitry, one or more characteristics of the current ECAP signal. The method also includes comparing, by the processing circuitry, the one or more characteristics of the current ECAP signal to corresponding one or more characteristics of a baseline ECAP signal, and determining, by the processing circuitry, based on the comparison, a migration state of the electrodes providing the electrical stimulation. Additionally, the method includes outputting, based on the migration state, an alert indicative of migration of the electrodes.

An example computer readable medium comprising instructions that, when executed, cause an implantable medical device to detect, via sensing circuitry, after delivery of an electrical stimulation pulse, a current ECAP signal and determine, by processing circuitry, one or more characteristics of the current ECAP signal. The instructions also cause the implantable medical device to compare, by the processing circuitry, the one or more characteristics of the current ECAP signal to corresponding one or more characteristics of a baseline ECAP signal, and determine, by the processing circuitry, based on the comparison, a migration state of the electrodes providing the electrical stimulation. Further, the instructions cause the implantable medical device to output, based on the migration state, an alert indicative of migration of the electrodes.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
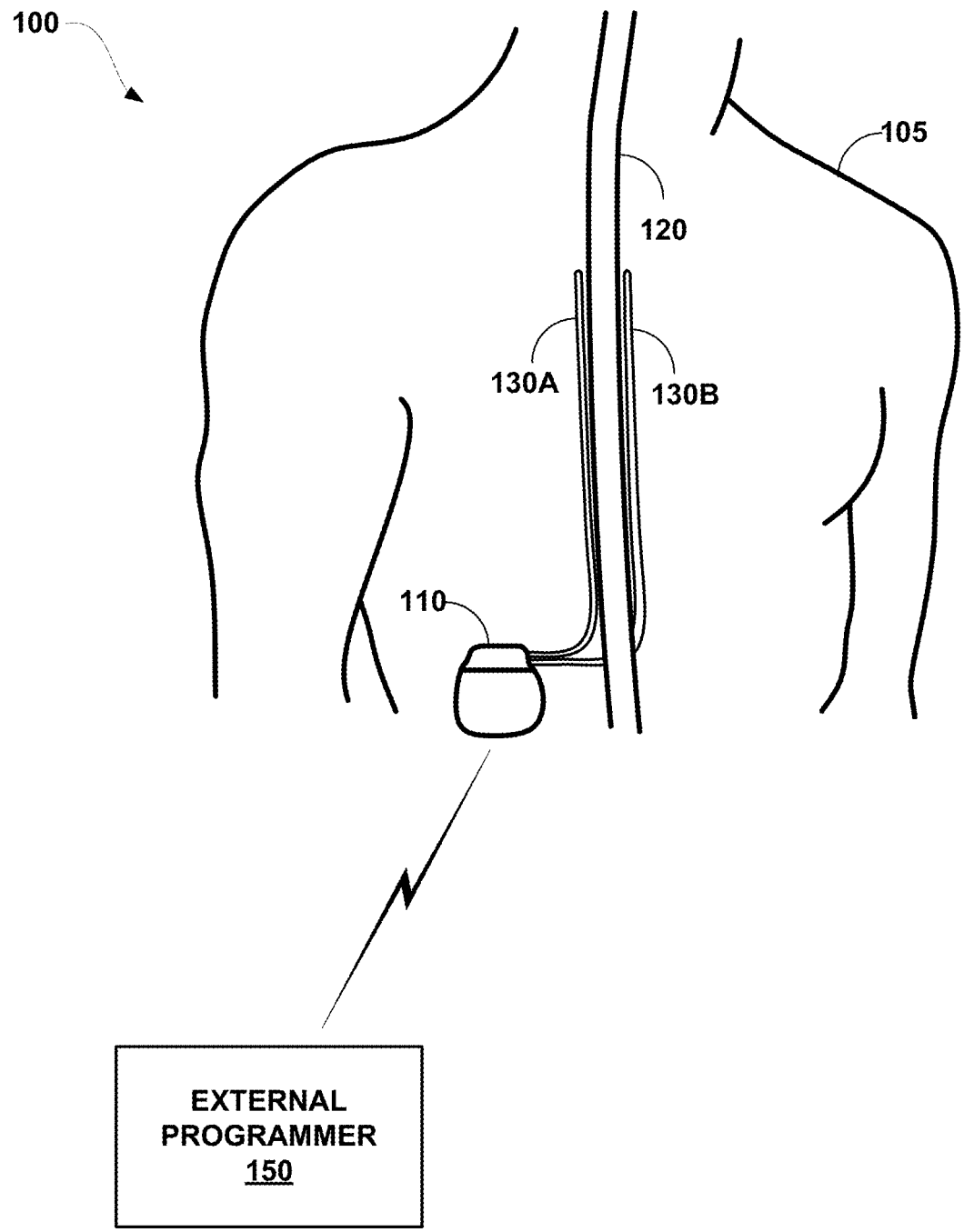
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques to detect lead migration based on one or more characteristics of evoked compound action potentials (ECAPs). Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. Electrodes implanted in a patient are positioned to provide effective therapy based on the stimulation parameters. However, electrodes may migrate, or move with respect to target tissue over time. For example, patients implanted with percutaneous leads may experience lead migration over time. Migration of leads may result in less effective treatment because less of the stimulation is applied to the target location and/or more stimulation is applied to other tissues that can cause side effects. Because lead migration may gradually progress, a patient may not notice the decrease in stimulation until the therapy substantially stops providing benefits.

ECAPs are a measure of neural recruitment because each ECAP signal represents the superposition of electrical potentials generated from a population of axons firing in response to an electrical stimulus (e.g., a stimulation pulse). The ECAP may be detectable as being a separate event from the stimulus itself, and the ECAP may reveal characteristics of the effect of the stimulus on the nerve fibers. That is, changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased. In other instances, changes in the latency between when the stimulus is delivered and when the ECAP is detected are used to assess electrode movement when, for example, multiple leads are employed. For example, two leads may be implanted next to each other and stimulation is delivered on one combination of electrodes, and the ECAP is sensed on another set of electrodes. If the latency changes in this example, shift between the leads is inferred. The amount of shift can be assessed by multiplying the conduction velocity (measured at baseline) by the latency timing change.

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). However, migration of leads that include the electrodes may cause a change in distance between the electrode and the target nerve. This change in distance can cause loss of effective therapy and/or side effects if the parameter values that define stimulation pulses are not adjusted to compensate for the change in distance. Additionally, lead migration may change the lead's position in relation to the vertebrae which may in turn change the intensity of the delivered stimulation.

As described herein, systems, devices, and techniques are described for determining migration of leads based on one or more evoked compound action potential (ECAPs) signals sensed from a patient. As discussed above, when the lead migrates from its original position. For example when electrodes implanted along the spinal column may partially or fully migrate in a lateral direction, the distance between implanted electrodes and target nerves changes. Additionally, in some examples, shielding from bone on the other side of the lead can change the effective electrical field and intensity directed to the spinal cord. For example when, electrodes implanted along the spinal column may partially or fully migrate in a longitudinal direction, causing distance between electrodes and vertebrae (e.g., the lamina of the vertebrae, etc.) to change due to bone narrowing/widening the epidural space. Therefore, a characteristic value of the ECAP signal changes according to the stimulation pulse that evoked the ECAP signal and the distance between the electrodes and the nerves.

An implantable medical device (IMD) may leverage the relationship between stimulation pulse parameters and the characteristic of the ECAP signal to detect lead migration. Initially, the IMD establishes a baseline ECAP signal elicited from a stimulus having a defined pulse width and frequency when electrodes are known to be proximate the target of electrical stimulation. For example, the ECAP signal may be captured when an implantable medical device (IMD) is implanted. From time-to-time, the IMD may collect one or more ECAP signals elicited by respective stimulus pulses according to an amplitude sweep with the defined pulse width and frequency. For example, the IMD may collect one or more ECAP signals periodically at a predetermined time (e.g., hourly, daily, weekly, etc.) or aperiodically (e.g., at the beginning of each stimulation session, in response to patient input indicative of changes in perception of therapy, inertia sensor measurements indicative of trauma, etc.) when the patient is likely to be in substantially the same position, such as 3 A.M. The IMD compares one or more characteristics of the captured ECAP signal to the corresponding one or more characteristics of the baseline ECAP signal to detect a change indicative of migration of the electrodes and thus migration of the leads. In some examples, because posture may temporarily effect the location of the electrodes compared to the stimulation target, the IMD may detect posture of the patient to distinguish between temporary changes from the baseline that may be due to posture and change in the baseline that may be due to lead migration. As described below, to determine whether the change in ECAP signal is indicative of migration lead, the IMD may analyze one or more characteristics of the captured ECAP signal. For example, while the peak-to-peak amplitude of the ECAP signal may not change (e.g., the amplitude between adjacent positive and negative peaks), the relative contributions of a peak and a valley of the ECAP signal may change. Or, in some examples, the latency between the leading edge of the stimulation pulse and the occurrence of a particular trough or peak of the ECAP may change. When the change in the components (e.g., the ration of the peak and the valley, etc.) of the ECAP signal exceeds (e.g., is greater than) a threshold, the IMD may provide an alert. The alert may trigger, for example, an adjustment to stimulation provided by the electrodes to compensate for the migration of the lead from the target location. The IMD, an external programmer, or a user may determine a change to one or more stimulation parameter values to adjust the stimulation and accommodate for the migration of the lead.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in the example of FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to detect whether leads 130 have migrated from their implanted location. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads.

In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

In some examples, IMD 110 may deliver stimulation pulses that contribute to therapy perceived by patient 105. IMD 110 may detect ECAP signals elicited by these stimulation pulses. In other examples, stimulation pulses configured to provide therapy may prevent IMD 110 from detecting ECAP signals (e.g., because the pulse width of the stimulation pulses are long enough to interfere with propagating ECAP signals. Therefore, if control pulses (e.g., pulses that may or may not contribute to therapy) separate from the informed pulses configured to provide therapy are needed to elicit a detectable ECAP signal, system 100 may employ an ECAP test stimulation program that defines stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. The stimulation defined by each ECAP test stimulation program may not be intended to provide or contribute to therapy for the patient, but the patient may perceive the control pulses in some examples. In addition, the ECAP test stimulation program may define the control pulses used for each sweep of pulses that are used to detect a change in an ECAP signal that is indicative of the associated lead having migrated from its original position.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced adjacent to spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which causes a tingling sensation that may reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended to detect migration of leads 130 via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

As described herein, IMD 110 may be configured to detect ECAP signals which are representative of the number of nerve fibers activated by a delivered stimulation signal (e.g., a delivered pulse). Additionally, IMD 110 may be configured to compare the ECAP signals to a baseline ECAP signal to detect whether one or more of leads 130 have migrated away from target area for stimulation. When IMD 110 is initially installed and leads 130 are implanted, IMD 110 may be configured to provide ECAP stimulation and detect ECAP signals to establish the baseline ECAP signal.

In some examples, IMD 110 may detect ECAP signals from pulses delivered for the purpose of providing therapy to the patient. In other examples, the pulses configured to provide therapy to the patient may interfere with the detection of the ECAP signals. In this manner, the therapy pulses may be referred to as informed pulses because the parameter values that define the informed pulses may be determined by IMD 110 according to ECAP signals elicited from different control pulses.

In one example, each informed pulse may have a pulse width greater than approximately 300 µs, such as between approximately 300 µs and 1000 µs (i.e., 1 millisecond) in some examples. At these pulse widths, IMD 110 may not sufficiently detect an ECAP signal because the informed pulse is also detected as an artifact that obscures the ECAP signal. When pulses intended to provide therapy have these longer pulse widths, IMD 110 may deliver control stimulation in the form of control pulses in order to detect ECAP signals. The control pulses may have pulse widths of less than the interfering therapy pulses (e.g., less than approximately 300 µs), such as a bi-phasic pulse with each phase having a duration of approximately 100 µs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs). In other examples, a biphasic pulse may have a positive phase lasting 120 μs, a negative phase lasting 120 μs, and an interphase interval lasting 30 μs defines a pulse width of 270 μs.

As described below, IMD 110 may be configured to detect migration of one or more of leads 130 from a target area of stimulation. Initially, IMD 110 is configured to capture a baseline ECAP signal to use to detect migration of one or more of leads 130 from a target area of stimulation. The target area may be a target tissue or nerve portion, or the target area may be an initial area of tissue for which stimulation was initially programmed. In some examples, IMD 110 may, as described below, use signals indicative of the posture of the patient to establish the baseline ECAP signal such that subsequent test ECAP signals are captured when the patient in in the same or similar posture. In some examples, IMD 110 is configured to record multiple baseline ECAP signals using different combinations of electrodes on a lead (e.g., lead 130A). As a lead migrates, different electrode combinations may be effected differently. For example, changes in proximity to the lamina may cause some electrode combinations to change relatively more than other electrode combinations base on how the lead migrates to areas with less space due between the lamina and the dura mater (e.g., the electrodes electric field may change due to proximity of electrodes to bone, etc.). Changes in one or more characteristics of subsequent ECAP signals may be indicative that electrodes of leads 130 are not positioned in the target location for stimulation. Periodically, IMD 110 performs an ECAP test stimulation program to detect one or more ECAP signals for a comparison to the baseline ECAP signal(s) (e.g., comparing one or more characteristics of the detected ECAP signal to the corresponding one or more characteristics of the baseline ECAP signal, etc.). IMD 110 may perform the ECAP test stimulation program at a day and time set via external programmer. For example, IMD 110 may perform the ECAP test stimulation program hourly, daily, weekly, or in response to a trigger event. The ECAP test stimulation program may be scheduled to coincide when patient 105 is, for example, sleeping to minimize the effects of difference in posture on the capture ECAP signal. In some examples, IMD 110 detects the posture of patient 105 before perform the ECAP test stimulation program to determine the effect of posture on the captured ECAP signal and/or to delay the ECAP test stimulation program until the posture of patient 105 is suitable for detecting whether one or more of leads 103 have migrated (e.g., when the patient is lying substantially horizontally, etc.). In some such examples, IMD 110 uses signals from an inertial sensor (e.g., an accelerometer, a gyroscope, etc.) to detect the posture of patient 105. Additionally or alternatively in some examples, IMD 110 performs a second ECAP test simulation program with a series of ECAP pulses to detect the posture of patient 105. Examples of using ECAP signals to detect the posture of patient 105 are described in U.S. patent application Ser. No. 16/721,576, entitled "Determining Posture State from ECAPS," filed Dec. 19, 2019, the contents of which is incorporated by reference in its entirety.

IMD 110 may determine that one or more of leads 130 have migrated from the target stimulation area when a difference of one or more characteristics between the baseline ECAP signal and the captured ECAP signal satisfies a threshold difference. In some examples, where different combinations of electrodes are used, IMD 110 determines that one or more of leads 130 have at least partially migrated from the target stimulation area when a difference of one or more characteristics between the one of the baseline ECAP signals and the corresponding captured ECAP signal satisfies (e.g., exceeds, etc.) a threshold. As described in more detail below, ECAP signals have different detectable components or characteristics that may change depending on the relationship of the location of the leads to the location of the axon to be stimulated, and/or the relationship of space between bone and the leads. As one or more of leads 130 migrate away from the axon over time, the detectable components or characteristics may change. For example, the peaks and valleys of the captured ECAP signal may change. Specifically, in some examples, the contribution of an amplitude of the peaks and valleys of the signals may change even when the total amplitude stays the same. IMD 110 may track a migration state that based upon a determination of whether one or more of leads 130 have migrated. The migration state may be a binary value (e.g., one or more leads 130 have migrated, no leads 130 have migrated, etc.) or a series of values that quantify lead migration. Upon detecting that the captured ECAP signal has changed compared to the baseline ECAP signal, IMD 110 provides an alert to, for example, a patient programmer. The alert may trigger a remedial action and/or prompt patient 105 to get the stimulation provide by IMD 110 adjust to compensate for the change in location of the electrodes. In some examples, IMD 110 may terminate delivery of stimulation therapy until stimulation parameters are adjusted to compensate for the lead movement.

Figure 2:
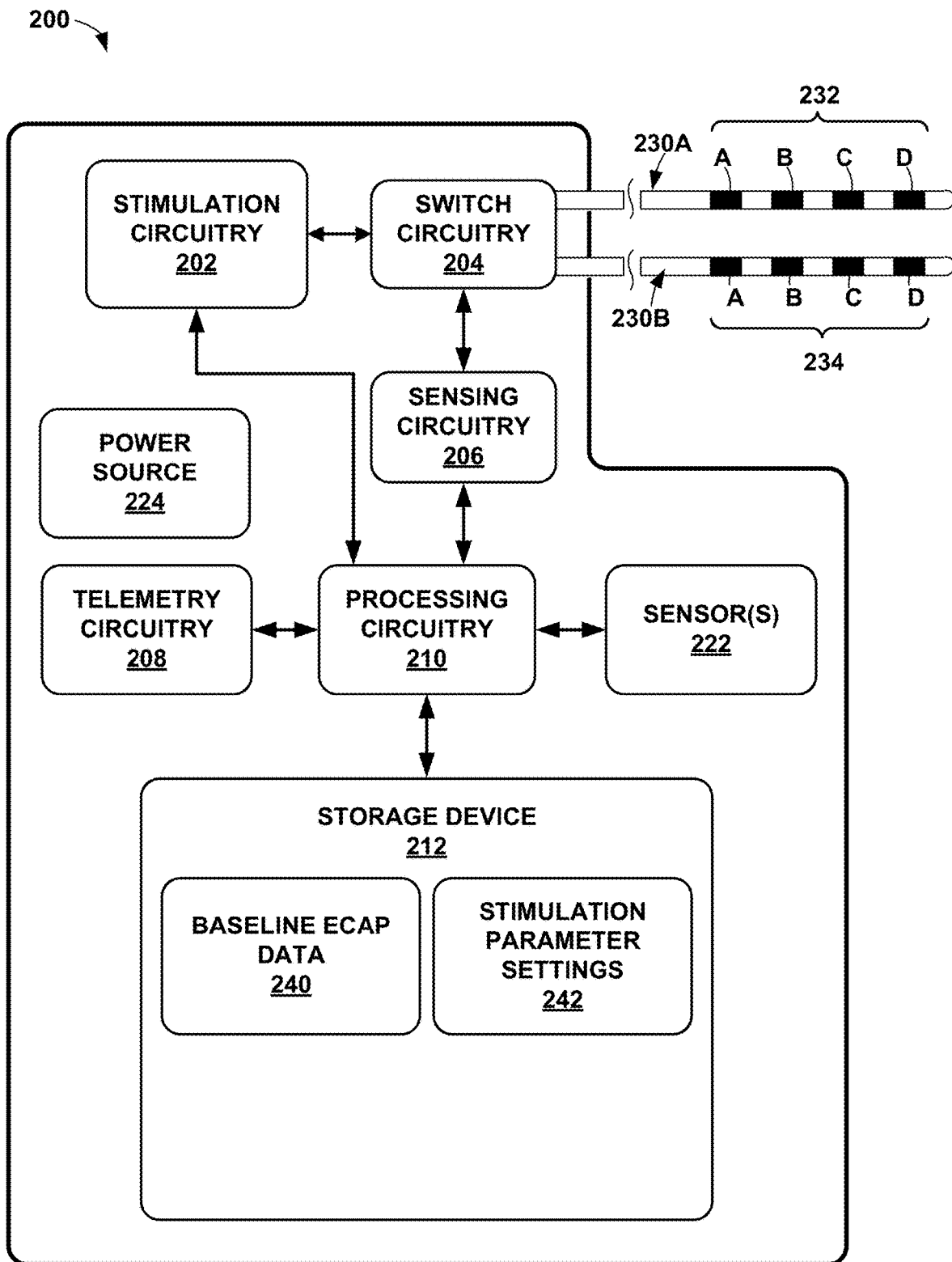
FIG. 2 is a block diagram illustrating an example configuration of components of an implantable medical device (IMD), in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores baseline ECAP data 240 and stimulation parameter settings 242 in separate memories within storage device 212 or separate areas within storage device 212. In some examples, stimulation parameter settings 242 may include stimulation parameter values (sometimes referred to as "sets of therapy parameters") for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape. In some examples, stimulation parameter settings 242 may store a primary set of therapy parameters for when leads 230 are in an implant location and a secondary set of therapy parameters for when one of leads 230 have migrated. Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store baseline ECAP data 240 and stimulation parameter settings 242. Baseline ECAP data 240 may store one or more baseline ECAP signals to be used to detect migration of leads 230 that cause electrodes 232 and/or electrodes 234 to move away from a target location for stimulation. For example, baseline ECAP data 240 may store a baseline ECAP signal for electrode A and B, A and C, A and D, B and C, B and D, and/or C and D. In some examples, baseline ECAP data 240 may store posture data to facilitate evaluating whether patient 105 is in a posture substantially similar to the posture when the baseline ECAP signal(s) was/were captured.

As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity or posture, and processing circuitry 210 may increase the frequency of control pulses and ECAP sensing in response to detecting increased patient activity or posture.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
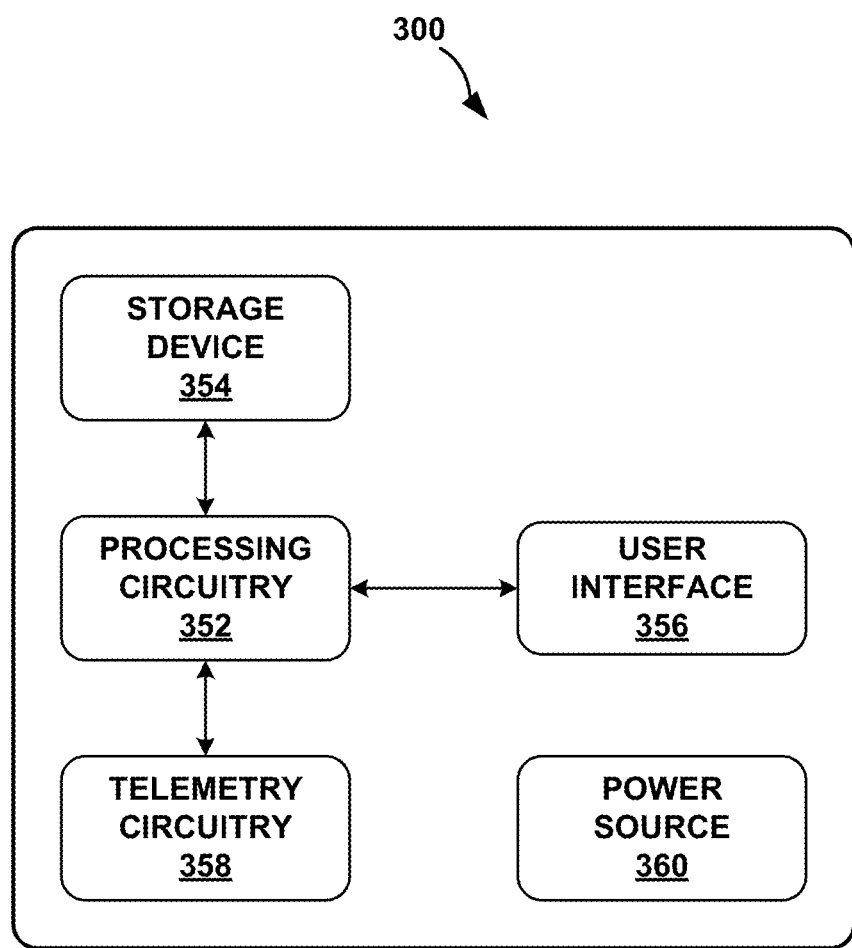
FIG. 3 is a block diagram illustrating an example configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, such as a representation of the baseline ECAP signal, a representation of the most recent captured ECAP signal, a measure of the latency between stimulation and ECAP detection, and/or an alert indicative of the migration state of leads 130. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation. During the calibration process of obtaining ECAP signals for different posture states, user interface 356 may present the posture state that the patient should assume, and user interface 356 may receive user input confirming that the patient is in the requested posture state. The calibration process may also incorporate radiographic data such as x-rays, fluorographs, CT scans, MR images or the like, and relate those data to the ECAP signal. In other examples, user interface 356 may receive user input indicating the posture state that the patient is in and generate the relationship of the detected ECAP characteristic values obtained during the calibration (e.g., the calibrated growth curve) for that indicated posture state.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs in response to an indication that the leads have migrated. For example, user interface 356 may receive an indication from the clinician to adjust a pulse width and/or an amplitude of the stimulation parameter values to compensate for the migration of the leads. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
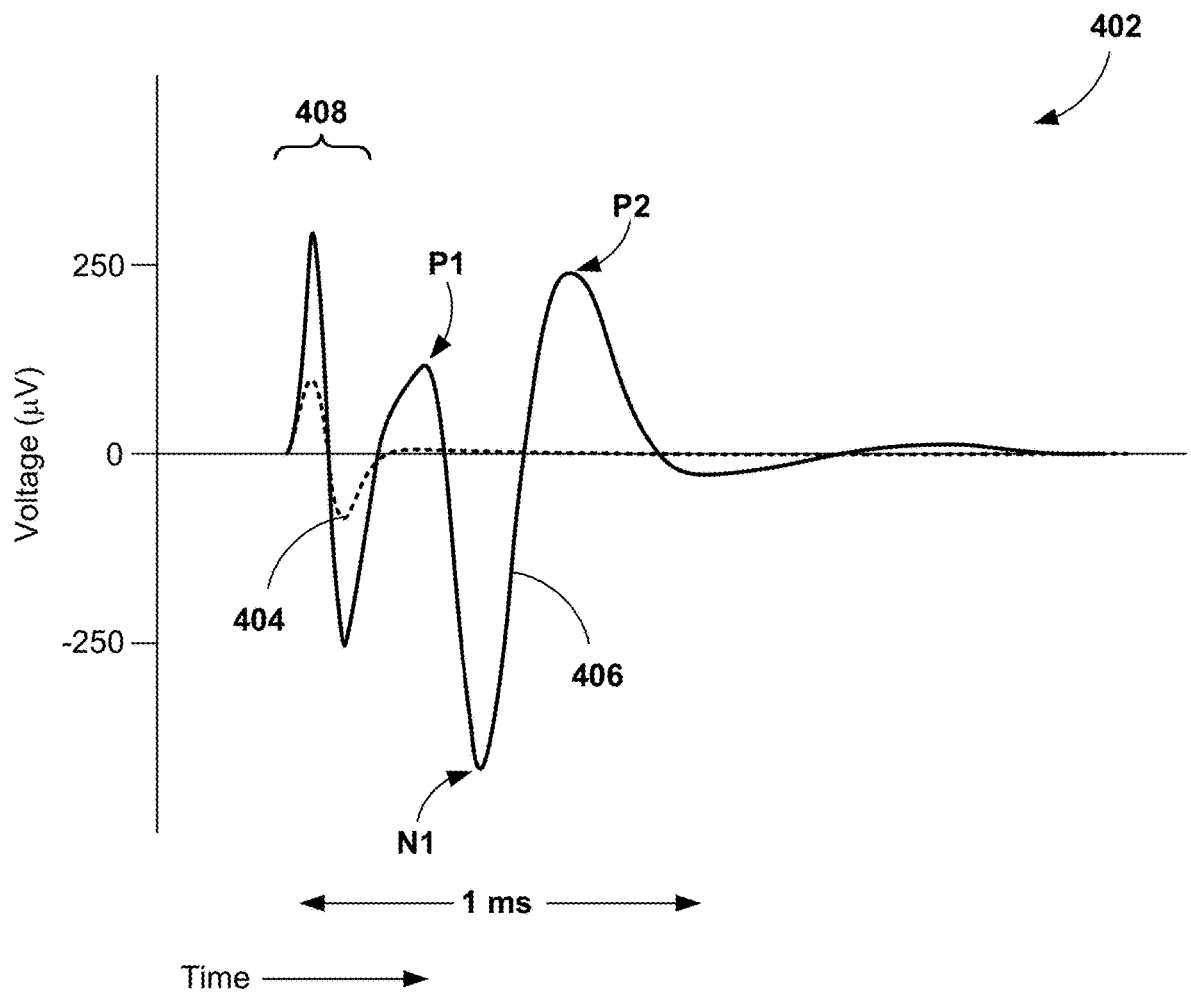
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse (e.g., a control pulse that may or may not contribute to a therapeutic effect for the patient). However, no propagating signal is detected after the artifact in ECAP signal 404 because the control pulse was sub-detection threshold.

In contrast to ECAP signal 404, ECAP signal 406 represents the voltage amplitude detected from a supra-detection threshold control pulse. Peaks 408 of ECAP signal 406 are detected and represent the artifact of the delivered control pulse. After peaks 408, ECAP signal 406 also includes peaks P1, N1 (sometime referred to as a valley), and P2, which are three typical peaks representative of propagating action potentials from an ECAP. In the illustrated example, duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact, a relatively large signal, impinges on P1. Additionally, the N1-P2 amplitude may be minimally affected by electronic drift in the signal. In other examples, the characteristic of the ECAP used to detect the posture state of the patient and/or control informed pulses may be an amplitude of P1, N1, or P2 with respect to neutral or zero voltage. In some examples, the characteristic of the ECAP may be a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two or more points in the ECAP signal, such as the slope between N1 and P2. For example, the characteristic may include the difference between two slopes (i.e. slope from N1 to P2 and the slope from P2 to end, etc.). In other examples, the characteristic of the ECAP may be the time between two points of the ECAP, such as the time between N1 and P2. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples. The amplitude of the ECAP signal generally increases with increased amplitude of the control pulse, as long as the pulse amplitude is greater than threshold such that nerves depolarize and propagate the signal.

As discussed herein, one or more characteristics of ECAP signal 406 (sometimes referred to as "characteristics of interest") may change from a baseline as electrodes move from the position in which the baseline was capture. For example, these characteristics of interest may include (i) the amplitude of P1, N1, and/or P2, (ii) the N1-P2 amplitude, (iii) a ratio of the relative contributions of N1 and P2, and/or (iv) the latency between an edge of the stimulation pulse and a feature of ECAP signal 406, etc. The latency is a measure of the interval between a leading or trailing edge of the stimulation pulse and a feature of the ECAP signal, such as P1, N1, or P2, etc. In some example, the latency may be referred to the "N1 latency" or "stimulation-to-N1" latency when the is a measure of the interval between a leading edge of the stimulation pulse and N1. IMD 110 may use changes to one or more characteristics of interest to detect when the lead and the corresponding electrodes have moved from their initial location. For examples, IMD 110 may determine that the lead has migrated when a ratio of the relative contributions of N1 and P2 changes by more than 25% compared to the ratio of the relative contributions of N1 and P2 in the baseline ECAP signal. As another example, IMD 110 may determine that the lead has migrated when the latency increases or decreases by more than 25 microseconds. In some examples, IMD 110 may determine that the lead has migrated when the ECAP signal for one or more electrode combinations change from the corresponding baseline ECAP signal. For example, IMD 110 may determine that the lead has migrated when at least a plurality, majority, or threshold number of ECAP signals for the electrode combinations sufficiently change from the corresponding baseline ECAP signal.

Figure 5A:
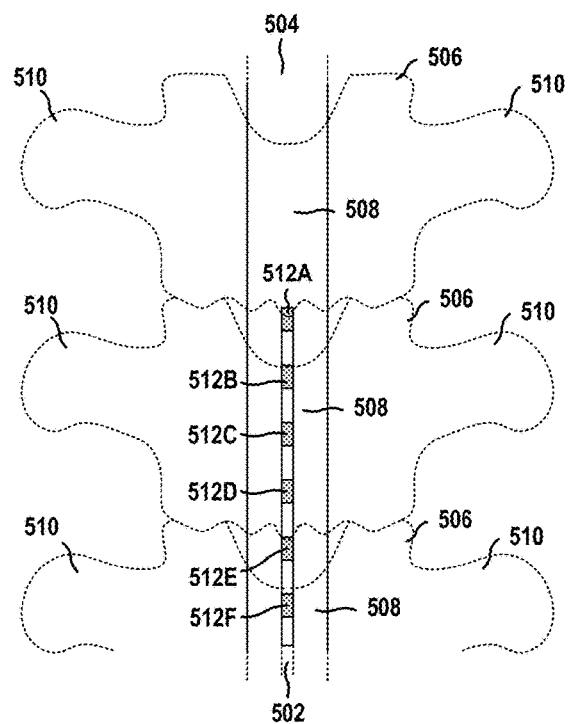
FIGS. 5A, 5B, and 5C illustrate a lead of an implantable medical device (IMD) implanted adjacent to a spinal cord, in accordance with one or more techniques of this disclosure.
Figure 5B:
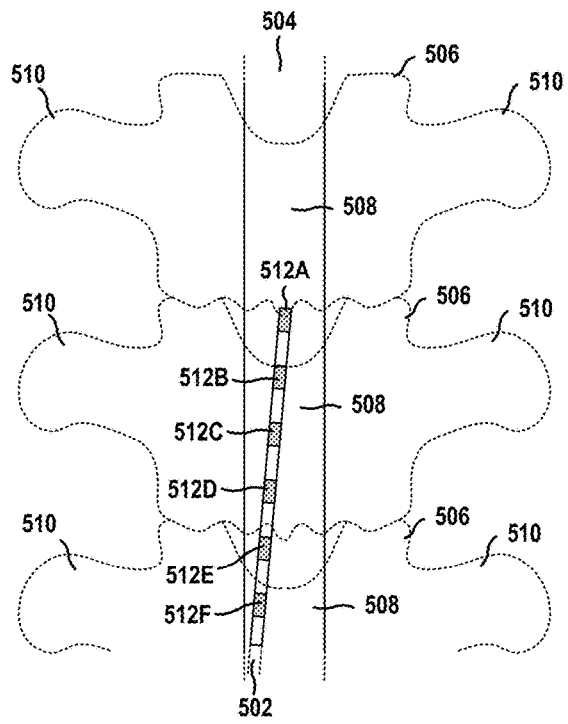
Figure 5C:
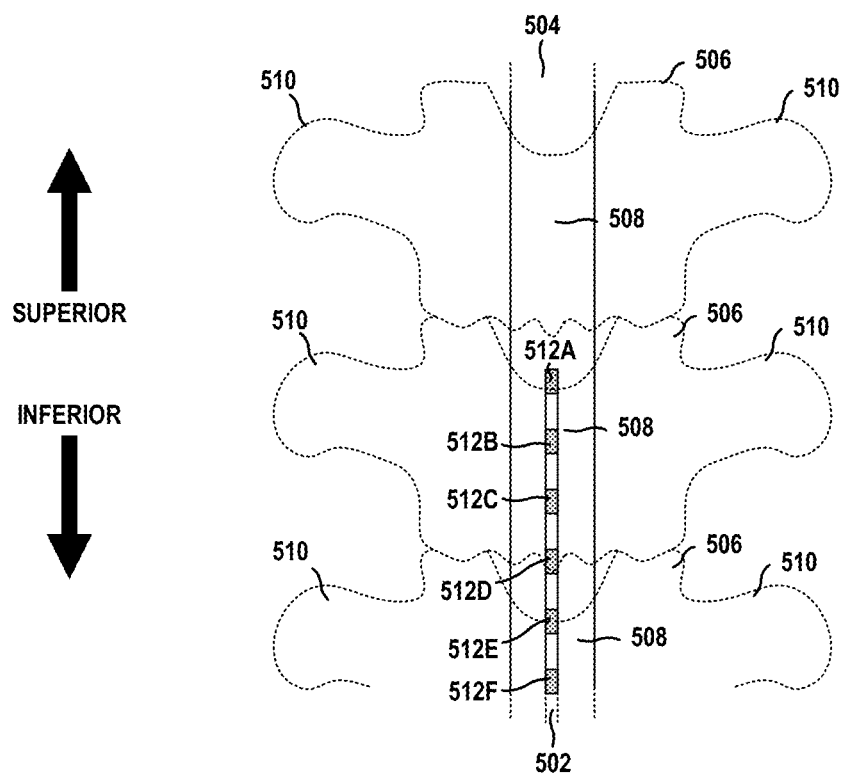

FIGS. 5A, 5B, and 5C illustrate example lead 502 of an implantable medical device (e.g., IMD 110) implanted adjacent to a spinal cord 504 in an epidural space, in accordance with one or more techniques of this disclosure. Lead 502 may be an example of leads 130 of FIG. 1. Examples in FIGS. 5A, 5B, and 5C illustrate vertebrae 506 with lamina 508 and transverse processes 510. For simplicity of illustration, FIGS. 5A, 5B, and 5C do not depict the spinous processes. In the illustrated example, lead 502 includes electrodes 512A-512F (collectively "electrodes 512"). Electrodes 512 may be examples of electrodes 232 and 234 of FIG. 2. FIG. 5A illustrates lead 502 in the location along spinal cord 504 at which lead 502 is implanted (e.g., the "implant location"). IMD 110 is programmed with one or more sets of therapy parameters (e.g., amplitude and pulse width, etc.) to provide effective therapy to patient 105 at the implant location. The effectiveness of the therapy parameters may wane as lead 502 (and the associated electrodes 512) migrates from implant location such that the therapy parameters may need to be adjusted to continue to provide effective therapy. Initially, IMD 110 captures baseline ECAP signal(s) when lead 502 is at the implant location.

FIG. 5B illustrates an example of lead 502 migrating from the implant location. In the illustrate example of FIG. 5B, at least a portion of lead 502 has laterally migrated such that one or more of electrodes 512 are no longer in a location provide effective therapy. When IMD 110 captures one or more ECAP signals (e.g., signals from different combinations of electrodes 512), at least one characteristic of at least one of the captured ECAP signals changes by a threshold amount that is indicative of lead migration. For example, the P1/N1 ratio of the ECAP signals captured using electrode 512E and electrode 512F may be, when compared to the corresponding baseline ECAP signal, indicative of lead migration.

FIG. 5C illustrates another example of lead 502 migrating from the implant location. Lead 502 may additionally or alternatively migrate longitudinally to be superior or inferior to the implant position. In the illustrate example of FIG. 5B, lead 502 has longitudinally migrated in the inferior direction such that one or more of electrodes 512 are no longer in a location provide effective therapy. In the illustrated example, lead 502 has migrated such that one or more electrodes 512 are in different positions relative to lamina 508. As lamina 508 extends of the top of vertebrae 506 to the bottom of vertebrae 506, lamina 508 is angled such that it is closer to spinal cord 504 at the top than at the bottom. Proximity to bone (e.g., lamina 508, etc.) may influence the characteristics of ECAP signals. For examples, the bone may affect electrical field and/or impedance, affecting stimulation signals, even if migration does not cause lead 502 to change position relative to the axon. In such a manner, IMD 110 may detect longitudinal movement of lead 502. When ECAP captures one or more ECAP signals (e.g., signals from different combinations of electrodes 512), at least one characteristic of at least one of the captured ECAP signals changes a threshold amount that is indicative of lead migration. For example, the P2 of the ECAP signals captured using electrode 512A and electrode 512B may be, when compared to the corresponding baseline ECAP signal, indicative of lead migration.

Figure 6A:
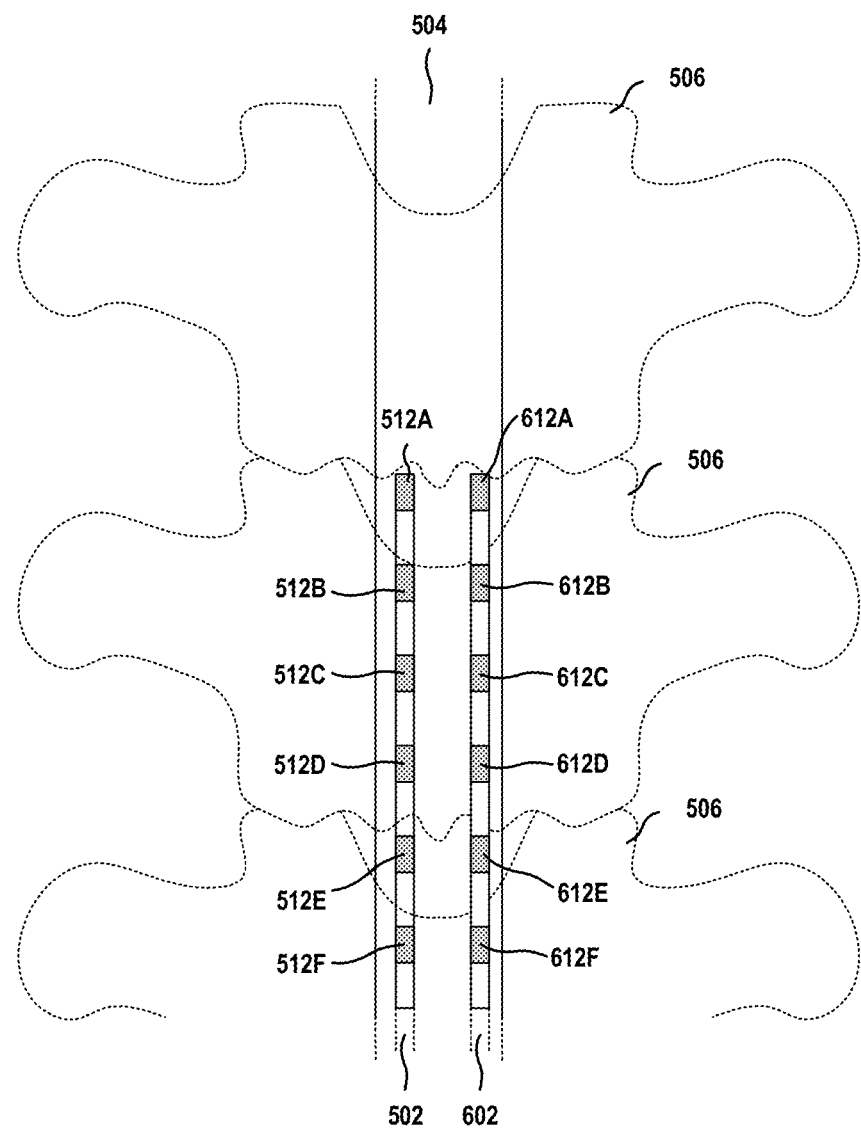
FIGS. 6A and 6B illustrate leads of an implantable medical device (IMD) implanted adjacent to a spinal cord, in accordance with one or more techniques of this disclosure.
Figure 6B:
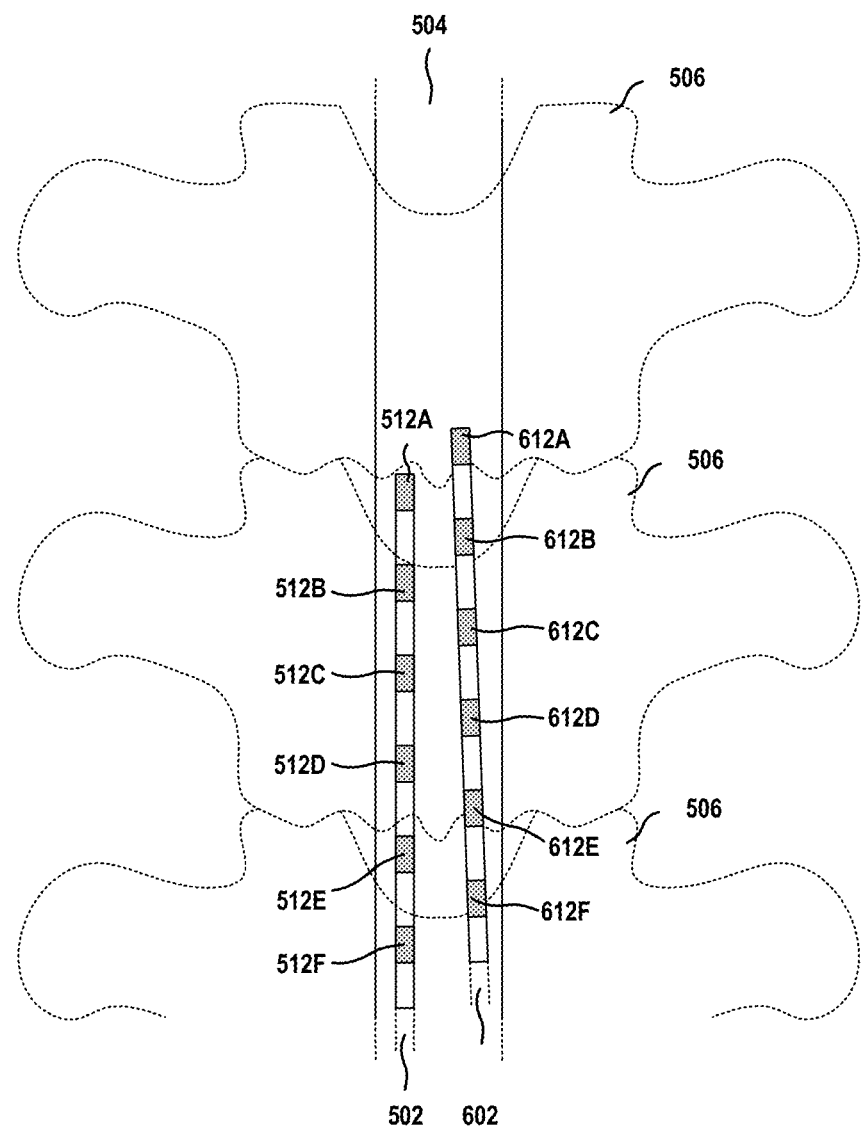

FIGS. 6A and 6B illustrate multiple leads 502 and 602 of IMD 110 implanted adjacent to spinal cord 504, in accordance with one or more techniques of this disclosure. Leads 502 and 602 may be an example of leads 130 of FIG. 1. Examples in FIGS. 6A and 6B illustrate vertebrae 506. Stimulus may be delivered on electrodes 512A and 512B of lead 502 and 612A and 612B of lead 602. The ECAP may be sensed on electrodes 512E and 512F of lead 502 and 612E and 612F of lead 602. FIG. 6A illustrated leads 502 and 602 at the implanted location. FIG. 6B illustrates lead 602 migrating such that the relationship between lead 502 and lead 602 changes. The stimulus from both leads 502 and 602 may result in an ECAP such that migrate of one or more of leads 502 and 602 relative to each other may cause the characteristics of the ECAP to change. For example, the stimulation to N1 latency may increase or decrease. If the latency changes, IMD 110 may determine that there has been a shift by at least one of leads 502 and 602. In some examples, the amount of shift can be assessed by multiplying the conduction velocity (measured at baseline) by the latency timing change.

Figure 7A:
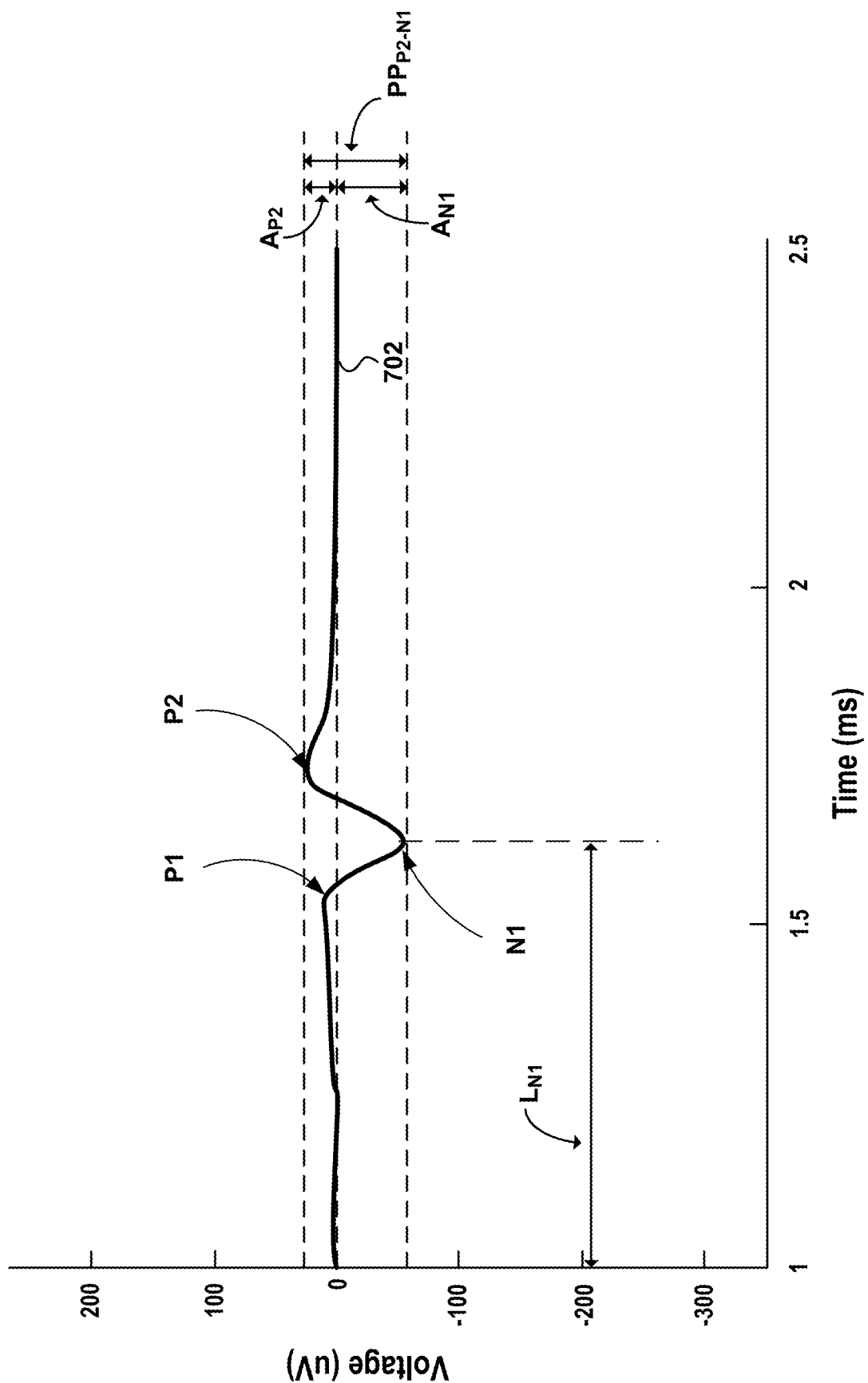
FIGS. 7A, 7B, and 7C are graphs of example evoked compound action potentials (ECAPs) sensed for respective stimulation pulses with leads of an implantable medical device (IMD) in different positions, in accordance with one or more techniques of this disclosure.
Figure 7B:
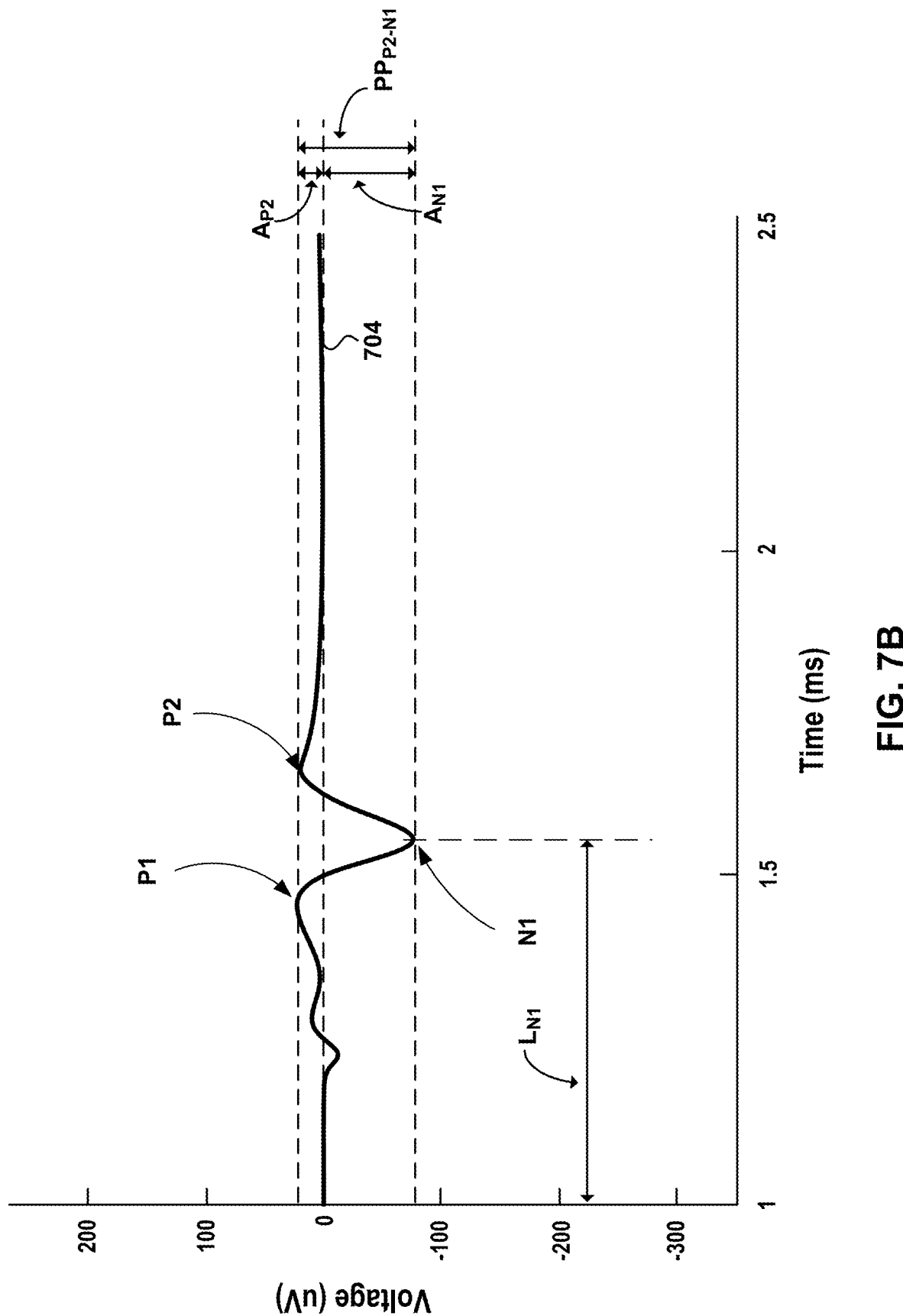
Figure 7C:
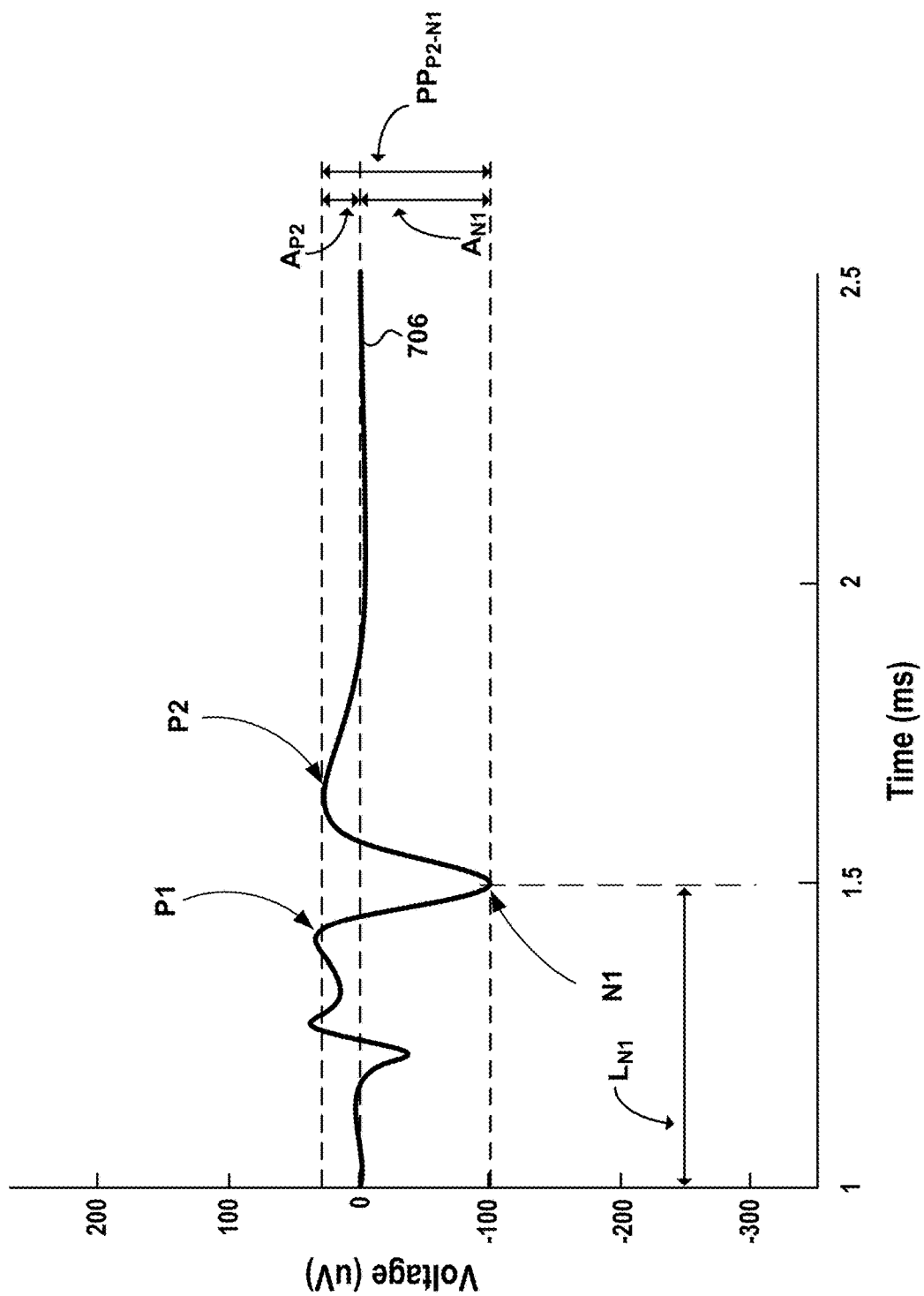

FIGS. 7A-7C are graphs of example ECAP signals sensed for respective stimulation pulses with leads (e.g., leads 130 of FIG. 1, lead 502 of FIG. 5, etc.) of IMD 110 in different positions (e.g., the implant location, different migration locations, etc.), in accordance with one or more techniques of this disclosure. FIG. 7A-7C illustrate example characteristics that may be used to detect when a lead has migrated from the implant location. After capturing the ECAP signal, IMD 110 may extract a P2 amplitude ($A_{P2}$), an N1 amplitude ($A_{N1}$), a peak-to-peak voltage from N1 to P2 ($PP_{P2-N1}$), and/or a latency from the stimulation to N1 ($L_{N1}$), etc. While these characteristics are specifically described, IMD 110 may extract other characteristics (e.g., P1 amplitude, a peak-to-peak voltage from P1 to N1, etc.) to facilitate detecting whether the lead has migrated. IMD 110 may use one or more of these characteristics and/or a relationship derived from these characteristics to detect migration. For example, IMD may use changes in $A_{P2}$. In some examples, IMD 110 detect lead migration based on a change in relative contribution to the peak-to-peak voltage from P2 to N1, for example, by deriving a ratio between these characteristics, such as $A_{P2}$ divided by $A_{N1}$ (e.g., the ratio of P2 to N1), and or $A_{P2}$ divided by PPP2-N1 (e.g., the ratio of P2 to the peak-to-peak voltage from P2 to N1).

FIG. 7A illustrates an example baseline ECAP signal 702 captured by IMD 110 after leads 130 are implanted. IMD 110 may store the baseline ECAP signal and/or may store one or more characteristics used to detect lead migration. FIG. 7B illustrates an example ECAP signal 704 captured after baseline ECAP signal 702 was captured by IMD 110. In the illustrated example, characteristics of ECAP signal 704 have changed compared to the characteristics of baseline ECAP signal 702. FIG. 7C illustrates another example ECAP signal 706 captured after baseline ECAP signal 702 was captured by IMD 110. In the illustrated example, characteristics of ECAP signal 706 have changed compared to the characteristics of baseline ECAP signal 702 such that IMD 110 determines that the lead has migrated For example, IMD 110 may base the determination on the change in the relative contribution of $A_{N1}$ to the peak-to-peak voltage from N1 to P2. As another example, IMD 110 may based the determination on in increase in timing of $L_{N1}$.

Figure 8:
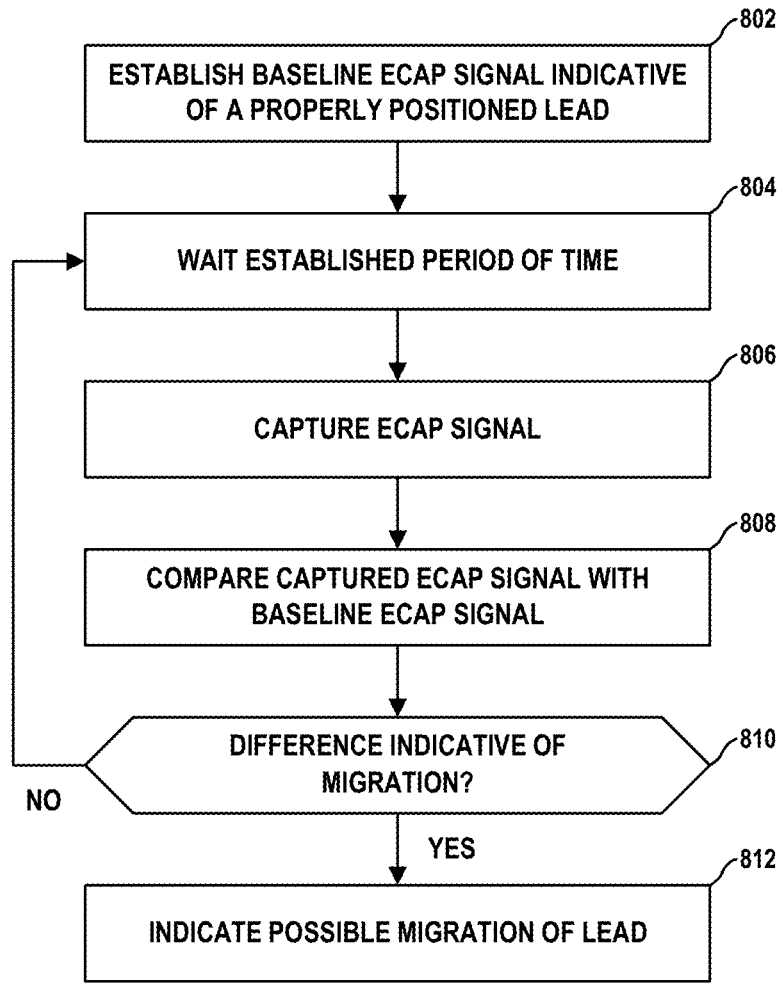
FIG. 8 is a flowchart of an example method to detect lead migration, in accordance with one or more techniques of this disclosure.

FIG. 8 is a flowchart of an example method to detect lead migration, in accordance with one or more techniques of this disclosure. Initially, IMD 110 establishes a baseline ECAP signal (e.g., baseline 702 of FIG. 7A, etc.) indicative of a properly positioned lead (802). For example, IMD 110 may establish a baseline ECAP signal after a set of therapy parameters is set or adjusted for the patient by external programmer 300. IMD 110 waits an established period of time (804). IMD 110 may periodically capture an ECAP signal. For example, IMD 110 may be configured to capture an ECAP signal for comparison every day at a certain time when patient 105 is likely to be resting or otherwise lying flat (e.g., in a posture conducive to detecting migration, etc.). IMD 110 delivers a stimulation pulse and subsequently captures the ECAP signal (806). In some examples, IMD 110 may first determine, based on inertial sensor data, whether patient 105 is in an appropriate posture for a representative ECAP signal to be captured. For example, IMD 110 may, based on measurements form inertial sensors, determine whether the patient is standing vertically or lying down horizontally before delivering the stimulation pulse that will be used to capture the ECAP signal.

IMD 110 compares one or more characteristics (e.g., the characteristics described in FIGS. 7A, 7B, and 7C above) of the captured ECAP signal with one or more characteristics of the baseline ECAP signal (808). For example, IMD 110 may compare the P2/N1 ratio of the captured ECAP signal to the P2/N1 ratio of the baseline ECAP signal. IMD 110 determines whether the difference of the compared characteristics is indicative of lead migration (810). In one example, IMD 110 may determine that the difference of the compared characteristics is indicative of lead migration when the P2/N1 ratio of the captured ECAP signal changes by a threshold amount (e.g., 10%, 25%, 33%, etc.) compared to the P2/N1 ratio of the baseline ECAP signal. When the difference is indicative of lead migration ("YES" branch of 810), IMD 110 provides an indication of possible migration of the lead (812). For example, IMD 110 may provide and alert to external programmer 300 so that external programmer 150, other device, or a user can adjust one or more stimulation parameter values to compensate for the migration. Additionally or alternatively, in some examples, IMD 110 may terminate therapy until stimulation parameter values are adjusted and/or until receiving an input from the patient to continue therapy. Additionally or alternatively, in some examples, IMD 110 may switch from a first set of therapy parameters configured for when the leads are in the implant location to a second set of therapy parameters configured for when one or more of the leads have migrated. Otherwise, when the difference is not indicative of lead migration ("NO" branch of 810), IMD 110 waits the established period of time to capture the next ECAP signal (804).

The following examples are described herein.

Example 1A. A system comprises: sensing circuitry configured to sense an evoked compound action potential (ECAP) signal; and processing circuitry configured to: control the sensing circuitry to detect, after delivery of an electrical stimulation pulse, a current ECAP signal; determine one or more characteristics of the current ECAP signal; compare the one or more characteristics of the current ECAP signal to corresponding one or more characteristics of a baseline ECAP signal; determine, based on the comparison, a migration state of the electrodes delivering the electrical stimulation pulse; and output, based on the migration state, an alert indicative of migration of the electrodes.

Example 1B. The system of Example 1A, wherein the characteristics of the current ECAP include at least one of an amplitude of a first peak (P1), an amplitude of a second peak (N1), an amplitude of a third peak (P2), and a latency.

Example 1C. The system of Example 1B, wherein to compare the one or more characteristics of the current ECAP signal to the corresponding one or more characteristics of the baseline ECAP signal, processing circuitry is configured to compare a first latency of the baseline ECAP signal to a second latency of the current ECAP signal, the first and second latencies being a measure of an interval between an edge of a respective electrical stimulation pulse and one of P1, N1, or P2 of the respective ECAP signal.

Example 1D. The system of Example 1B, wherein to compare the one or more characteristics of the current ECAP signal to the corresponding one or more characteristics of the baseline ECAP signal, processing circuitry is configured to compare a first relative contribution of P2 to a peak-to-peak amplitude between P2 and N1 of the baseline ECAP signal to a second relative contribution of P2 to the peak-to-peak amplitude between P2 and N1 of the current ECAP signal.

Example 1E. The system of any of Example 1A through Example 1D, wherein the migration state is indicative of lead migration when a difference between the one or more characteristics of the current ECAP signal and the corresponding one or more characteristics of the baseline ECAP signal exceeds a threshold value.

Example 1F. The system of any of Example 1A through Example 1E, wherein the processing circuitry is configured to: store the one or more characteristics of the current ECAP signal in memory: and determine a subsequent migration state based on the one or more characteristics of the current ECAP signal stored in the memory.

Example 1G. The system any of Example 1A through Example 1F, further comprising telemetry circuitry configured to transmit the alert to an external programmer, the alert configured to cause the external programmer to adjust a set of therapy parameters to compensate for the migration state of the electrodes.

Example 1H. The system of Example 1A, wherein the current ECAP signal is a first current ECAP signal detected by the sensing circuitry using a first combination of the electrodes, and wherein the processing circuitry is configured to control the sensing circuitry to detect, after delivery of a second electrical stimulation pulse, a second current ECAP signal using a second combination of the electrodes.

Example 1I. The system of Example 1H, wherein the baseline ECAP signal is a first baseline ECAP signal detected by the sensing circuitry using the first combination of the electrodes, and wherein the processing circuitry is configured to compare the one or more characteristics of the second current ECAP signal to corresponding one or more characteristics of a second baseline ECAP signal detected by the sensing circuitry using the second combination of the electrodes.

Example 1J. The system of Example 1H, wherein the processing circuitry is configured to set the migration state to indicate lead migration when one of: (a) a first difference between the one or more characteristics of the first current ECAP signal and the corresponding one or more characteristics of the first baseline ECAP signal satisfies a threshold value, or (b) a second difference between the one or more characteristics of the second current ECAP signal and the corresponding one or more characteristics of the second baseline ECAP signal satisfies the threshold value.

Example 1K. The system of any of Example 1A through Example 1F, wherein the processing circuitry is configured to: detect a current posture of a patient; determine that the current posture is equivalent to a target posture detected when the baseline ECAP signal was sensed; and responsive to determining that the current posture is equivalent to the target posture, control the sensing circuitry to detect the current ECAP signal.

Example 1L. The system of any of Example 1A through Example 1F, wherein the electrical stimulation pulse is generated with a first set of therapy parameters, and wherein the processing circuitry is configured to, based on the migration state, switch the first set of therapy parameters with a second set of therapy parameters to cause a subsequent electrical stimulation pulse to be generated with the second set of therapy parameters.

Example 1M. The system of Example 1A, further comprising an implantable medical device comprising the sensing circuitry and the processing circuitry.

Example 2A. A method to detect migration of leads coupled to an implantable medical device, the method comprising: detecting, via sensing circuitry, after delivery of an electrical stimulation pulse, a current ECAP signal; determining, by processing circuitry, one or more characteristics of the current ECAP signal; comparing, by the processing circuitry, the one or more characteristics of the current ECAP signal to corresponding one or more characteristics of a baseline ECAP signal; determining, by the processing circuitry, based on the comparison, a migration state of the electrodes providing the electrical stimulation; and outputting, based on the migration state, an alert indicative of migration of the electrodes.

Example 2B. The method of Example 2A, wherein the characteristics of the current ECAP include at least one of an amplitude of a first peak (P1), an amplitude of a second peak (N1), an amplitude of a third peak (P2), and a latency.

Example 2C. The method of Example 2B, wherein comparing the one or more characteristics of the current ECAP signal to the corresponding one or more characteristics of the baseline ECAP signal comprises comparing a first relative contribution of P2 to a peak-to-peak amplitude between P2 and N1 of the baseline ECAP signal to a second relative contribution of P2 to the peak-to-peak amplitude between P2 and N1 of the current ECAP signal.

Example 2D. The method of Example 2A, wherein the migration state is indicative of lead migration when a difference between the one or more characteristics of the current ECAP signal and the corresponding one or more characteristics of the baseline ECAP signal exceeds a threshold value.

Example 2E. The method of any of Example 2A through Example 2D, comprising storing the one or more characteristics of the current ECAP signal in memory; and determining a subsequent migration state based on the one or more characteristics of the current ECAP signal stored in the memory.

Example 2F. The method of any of Example 2A through Example 2E, comprising transmitting, by telemetry circuitry, the alert to an external programmer to cause the external programmer to adjust a set of therapy parameters to compensate for the migration of the electrodes.

Example 2G. The method of any of Example 2A through Example 2F, wherein the current ECAP signal is a first current ECAP signal detected by the sensing circuitry using a first combination of the electrodes, and wherein the method comprises detecting, by the sensing circuitry, after delivery of a second electrical stimulation pulse, a second current ECAP signal using a second combination of the electrodes.

Example 2H. The method of Example 2G, wherein the baseline ECAP signal is a first baseline ECAP signal detected by the sensing circuitry using the first combination of the electrodes, and wherein the method comprises comparing the one or more characteristics of the second current ECAP signal to corresponding one or more characteristics of a second baseline ECAP signal detected by the sensing circuitry using the second combination of the electrodes.

Example 2I. The method of Example 2G, comprising setting, by the processing circuitry, the migration state to indicate lead migration when either (a) a first difference between the one or more characteristics of the first current ECAP signal and the corresponding one or more characteristics of the first baseline ECAP signal satisfies a threshold value, or (b) a second difference between the one or more characteristics of the second current ECAP signal and the corresponding one or more characteristics of the second baseline ECAP signal satisfies the threshold value.

Example 2J. The method of any of Example 2A through Example 2I, comprising: detecting a current posture of a patient; determining that the current posture is equivalent to a target posture detected when the baseline ECAP signal was sensed; and responsive to determining that the current posture is equivalent to the target posture, controlling the sensing circuitry to detect the current ECAP signal.

Example 3. A computer readable medium comprising instructions that, when executed, cause an implantable medical device to: detect, via sensing circuitry, after delivery of an electrical stimulation pulse, a current ECAP signal; determine, by processing circuitry, one or more characteristics of the current ECAP signal; compare, by the processing circuitry, the one or more characteristics of the current ECAP signal to corresponding one or more characteristics of a baseline ECAP signal; determine, by the processing circuitry, based on the comparison, a migration state of the electrodes providing the electrical stimulation; and output, based on the migration state, an alert indicative of migration of the electrodes.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
   sensing circuitry configured to sense an evoked compound action potential (ECAP) signal; and
   processing circuitry configured to:
      control the sensing circuitry to detect, after delivery of an electrical stimulation pulse by implanted electrodes, a current ECAP signal;
      determine one or more characteristics of the current ECAP signal, wherein the one or more characteristics of the current ECAP signal comprises a second contribution of a first peak to a peak-to-peak amplitude between the first peak and a second peak of the current ECAP signal;
      receive one or more characteristics of a baseline ECAP signal, wherein the one or more characteristics of the baseline signal comprises a first contribution of the first peak to the peak-to-peak amplitude between the first peak and the second peak of the current ECAP signal;
      compare the second contribution of the first peak to the peak-to-peak amplitude of the current ECAP signal to the first contribution of the first peak to the peak-to-peak amplitude of the baseline ECAP signal;
      determine, based on the comparison, a migration state of the implanted electrodes that delivered the electrical stimulation pulse, wherein the migration state indicates at least one of a lateral migration state or a longitudinal migration state from a target implant location; and
      output, based on the migration state, an alert indicative of migration of the implanted electrodes from the target implant location.

2. The system of claim 1, wherein the characteristics of the current ECAP signal include at least one of an amplitude of the first peak (P1), an amplitude of the second peak (N1), an amplitude of a third peak (P2), or a latency.

3. The system of claim 2, wherein the processing circuitry is configured to compare a first latency of the baseline ECAP signal to a second latency of the current ECAP signal, the first and second latencies being a measure of an interval between an edge of a respective electrical stimulation pulse and one of P1, N1, or P2 of the respective ECAP signal, and determine, based on the comparison of the first latency and second latency and the comparison of the first contribution to the second contribution, the migration state of the implanted electrodes.

4. The system of claim 2, wherein the first peak is a P2 peak and the second peak is an N1 peak.

5. The system of claim 1, wherein the processing circuitry is configured to determine that the migration state is indicative of lead migration in response to a difference between the one or more characteristics of the current ECAP signal and the corresponding one or more characteristics of the baseline ECAP signal exceeding a threshold value.

6. The system of claim 1, wherein the processing circuitry is configured to:
   store the one or more characteristics of the current ECAP signal in memory: and
   determine a subsequent migration state based on the one or more characteristics of the current ECAP signal stored in the memory.

7. The system of claim 1, further comprising telemetry circuitry configured to transmit the alert to an external programmer, the alert configured to cause the external programmer to adjust at least one parameter value of a set of therapy parameters to compensate for the migration state of the implanted electrodes from the target implant location.

8. The system of claim 1, wherein the current ECAP signal is a first current ECAP signal detected by the sensing circuitry using a first combination of the electrodes, and wherein the processing circuitry is configured to control the sensing circuitry to detect, after delivery of a second electrical stimulation pulse, a second current ECAP signal using a second combination of the electrodes.

9. The system of claim 8, wherein the baseline ECAP signal is a first baseline ECAP signal detected by the sensing circuitry using the first combination of the electrodes, and wherein the processing circuitry is configured to compare the one or more characteristics of the second current ECAP signal to corresponding one or more characteristics of a second baseline ECAP signal detected by the sensing circuitry using the second combination of the electrodes.

10. The system of claim 9, wherein the processing circuitry is configured to set the migration state to indicate lead migration in response to one of: (a) a first difference between the one or more characteristics of the first current ECAP signal and the corresponding one or more characteristics of the first baseline ECAP signal satisfies a threshold value, or (b) a second difference between the one or more characteristics of the second current ECAP signal and the corresponding one or more characteristics of the second baseline ECAP signal satisfies the threshold value.

11. The system of claim 1, wherein the processing circuitry is configured to:
  detect a current posture of a patient;
  determine that the current posture is equivalent to a target posture detected when the baseline ECAP signal was sensed; and
  responsive to determining that the current posture is equivalent to the target posture, control the sensing circuitry to detect the current ECAP signal.

12. The system of claim 1, wherein the electrical stimulation pulse is generated with a first set of therapy parameters, and wherein the processing circuitry is configured to, based on the migration state, switch the first set of therapy parameters with a second set of therapy parameters to cause a subsequent electrical stimulation pulse to be generated with the second set of therapy parameters.

13. The system of claim 1, further comprising an implantable medical device comprising the sensing circuitry and the processing circuitry.

14. A method to detect migration of electrodes coupled to an implantable medical device, the method comprising:
  detecting, via sensing circuitry, after delivery of an electrical stimulation pulse by implemented electrodes, a current ECAP signal;
  determining, by processing circuitry, one or more characteristics of the current ECAP signal, wherein the one or more characteristics of the current ECAP signal comprises a second contribution of a first peak to a peak-to-peak amplitude between the first peak and a second peak of the current ECAP signal;
  receive one or more characteristics of a baseline ECAP signal, wherein the one or more characteristics of the baseline signal comprises a first contribution of the first peak to the peak- to-peak amplitude between the first peak and the second peak of the current ECAP signal;
  comparing, by the processing circuitry, the second contribution of the first peak to the peak-to-peak amplitude of the current ECAP signal to the first contribution of the first peak to the peak-to-peak amplitude of the baseline ECAP signal;
  determining, by the processing circuitry, based on the comparison, a migration state of the implanted electrodes providing the electrical stimulation pulse, wherein the migration state indicates at least one of a lateral migration state or a longitudinal migration state from a target implant location; and
  outputting, based on the migration state, an alert indicative of migration of the implanted electrodes from the target implant location.

15. The method of claim 14, wherein the characteristics of the current ECAP signal include at least one of an amplitude of the first peak (P1), an amplitude of the second peak (N1), an amplitude of a third peak (P2), or a latency.

16. The method of claim 15, the first peak is a P2 peak and the second peak is an N1 peak.

17. The method of claim 14, wherein the migration state is indicative of lead migration in response to a difference between the one or more characteristics of the current ECAP signal and the corresponding one or more characteristics of the baseline ECAP signal exceeding a threshold value.

18. The method of claim 14, comprising:
  storing the one or more characteristics of the current ECAP signal in memory; and
  determining a subsequent migration state based on the one or more characteristics of the current ECAP signal stored in the memory.

19. The method of claim 14, comprising transmitting, by telemetry circuitry, the alert to an external programmer to cause the external programmer to adjust at least one parameter value of a set of therapy parameters to compensate for the migration of the implanted electrodes from the target implant location.

20. The method of claim 14, wherein the current ECAP signal is a first current ECAP signal detected by the sensing circuitry using a first combination of the electrodes, and wherein the method comprises detecting, by the sensing circuitry, after delivery of a second electrical stimulation pulse, a second current ECAP signal using a second combination of the electrodes.

21. The method of claim 20, wherein the baseline ECAP signal is a first baseline ECAP signal detected by the sensing circuitry using the first combination of the electrodes, and wherein the method comprises comparing the one or more characteristics of the second current ECAP signal to corresponding one or more characteristics of a second baseline ECAP signal detected by the sensing circuitry using the second combination of the electrodes.

22. The method of claim 21, comprising setting, by the processing circuitry, the migration state to indicate lead migration in response to either (a) a first difference between the one or more characteristics of the first current ECAP signal and the corresponding one or more characteristics of the first baseline ECAP signal satisfies a threshold value, or (b) a second difference between the one or more characteristics of the second current ECAP signal and the corresponding one or more characteristics of the second baseline ECAP signal satisfies the threshold value.

23. The method of claim 14, comprising:
  detecting a current posture of a patient;
  determining that the current posture is equivalent to a target posture detected when the baseline ECAP signal was sensed; and
  responsive to determining that the current posture is equivalent to the target posture, controlling the sensing circuitry to detect the current ECAP signal.

24. A non-transitory computer readable medium comprising instructions that, when executed, cause an implantable medical device to:
  detect, via sensing circuitry, after delivery of an electrical stimulation pulse by implanted electrodes, a current ECAP signal;
  determine, by processing circuitry, one or more characteristics of the current ECAP signal, wherein the one or more characteristics of the current ECAP signal comprises a second contribution of a first peak to a peak-to-peak amplitude between the first peak and a second peak of the current ECAP signal;
  receive one or more characteristics of a baseline ECAP signal, wherein the one or more characteristics of the baseline signal comprises a first contribution of the first peak to the peak-to-peak amplitude between the first peak and the second peak of the current ECAP signal;

compare, by the processing circuitry, the second contribution of the first peak to the peak-to-peak amplitude of the current ECAP signal to the first contribution of the first peak to the peak-to-peak amplitude of the baseline ECAP signal;

determine, by the processing circuitry, based on the comparison, a migration state of the implanted electrodes providing the electrical stimulation pulse, wherein the migration state indicates at least one of a lateral migration state or a longitudinal migration state from a target implant location; and output, based on the migration state, an alert indicative of migration of the implanted electrodes from the target implant location.

\* \* \* \* \*